United States Patent [19]

Sarantakis

[11] 4,230,617
[45] Oct. 28, 1980

[54] SOMATOSTATIN ANALOGUES

[75] Inventor: Dimitrios Sarantakis, West Chester, Pa.

[73] Assignee: American Home Products Corporation, New York, N.Y.

[21] Appl. No.: 54,545

[22] Filed: Jul. 5, 1979

[51] Int. Cl.³ .................... C07C 103/52; C08L 37/00; A61K 37/00
[52] U.S. Cl. ................................ 260/112.5 S; 260/8; 424/177
[58] Field of Search ................... 260/112.5 S; 424/177

[56] References Cited

U.S. PATENT DOCUMENTS

| | | | |
|---|---|---|---|
| 4,077,952 | 3/1978 | Sarantakis | 260/112.5 S |
| 4,098,782 | 7/1978 | Sarantakis | 260/112.5 S |
| 4,104,267 | 8/1978 | Sarantakis | 260/112.5 S |
| 4,122,077 | 10/1978 | Sarantakis | 260/112.5 S |

OTHER PUBLICATIONS

Rivier et al., "Proceedings of the Fourteenth European Peptides Symposium" 437–444.

Primary Examiner—Delbert R. Phillips
Attorney, Agent, or Firm—Richard K. Jackson

[57] ABSTRACT

The polypeptides,

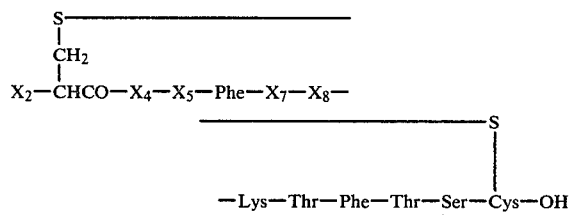

the linear precursor intermediates therefor or non-toxic acid addition salts thereof in which $X_2$ is $NH_2$, Ala-Gly-, Ala-D-Ala-, Gly-Gly-Gly-, lower alkanoyl or benzoyl;

$X_4$ is Arg, His, D-Arg or D-His;

$X_5$ is His, Tyr, Glu, D-His, D-Tyr or D-Glu;

$X_7$ is Trp, Tyr, Met or His;

and $X_8$ is Trp or D-Trp;

inhibit the release of growth hormone and are useful in the treatment of acromegaly and diabetes.

4 Claims, No Drawings

SOMATOSTATIN ANALOGUES

BRIEF SUMMARY OF THE INVENTION

This invention provides certain somatostatin analogues selectively modified in 4, 5, 7, and 8 positions, which are capable of suppressing release of growth hormone. Thus, this invention resides in a group of novel polypeptides which are useful in the treatment of acromegaly and diabetes. The linear precursors for the novel polypeptides, either protected or deprotected, form an additional aspect of the invention.

DETAILED DESCRIPTION OF THE INVENTION

In accordance with this invention there is provided a group of polypeptides with the ability to inhibit release of growth hormone (somatotropin), which polypeptides are represented by the formula:

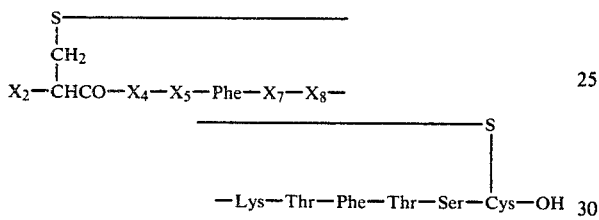

in which
$X_2$ is $NH_2$, Ala-Gly, Ala-D-Ala-, Gly-Gly-Gly-, lower alkanoyl or benzoyl;
$X_4$ is Arg, His, D-Arg, or D-His;
$X_5$ is His, Tyr, Glu, D-His, D-Tyr, or D-Glu;
$X_7$ is Trp, Tyr, Met, or His;
and
$X_8$ is Trp or D-Trp;
or a non-toxic addition salt thereof.

The non-toxic acid addition salts are pharmaceutically acceptable and are prepared from the polypeptide by conventional methods. Illustrative acids from which such salts are prepared include both organic and inorganic acids such as hydrochloric, hydrobromic, sulfuric, sulfonic, polyphosphoric, phosphoric, nitric, tartaric, fumaric, glycolic, citric, maleic, succinic, acetic, propionic, benzoic, ascorbic, and the like.

The lower alkanoyl N-terminal group embraces alkanoyl radicals of 2 to 6 carbon atoms, preferably the acetyl group.

In accordance with an additional aspect of this invention there is provided a group of novel linear precursor intermediates useful in the preparation of the polypeptides described above, of the formula:

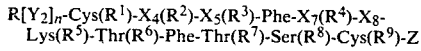

$R[Y_2]_n\text{-Cys}(R^1)\text{-}X_4(R^2)\text{-}X_5(R^3)\text{-Phe-}X_7(R^4)\text{-}X_8\text{-}$
$\text{Lys}(R^5)\text{-Thr}(R^6)\text{-Phe-Thr}(R^7)\text{-Ser}(R^8)\text{-Cys}(R^9)\text{-Z}$ in which
R is hydrogen, an α-amino protecting group, lower alkanoyl or benzoyl;
$R^1$ and $R^9$ are hydrogen or a thio protecting group;
$R^2$ is hydrogen or a protecting group for $N^g$ of Arg, or the $N^{im}$ of His;
$R^3$ is hydrogen or a protecting group for $N^{im}$ of His or the hydroxyl group of Tyr;
$R^4$ is hydrogen or a protecting group for the 1H indole nitrogen of Trp, the $N^{im}$ of His, or the hydroxyl group of Tyr;
$R^5$ is hydrogen or an amino protecting group;
$R^6$ is hydrogen or a hydroxyl protecting group for Thr;
$R^7$ and $R^8$ are hydrogen or a hydroxyl protecting group for Thr and Ser;
where
$Y_2$ is Ala-Gly-, Ala-D-Ala- or Gly-Gly-Gly-;
n is 0 or 1;
$X_4$ is Arg, His, D-Arg, or D-His;
$X_5$ is His, Tyr, Glu, D-His, D-Tyr, or D-Glu;
$X_7$ is Trp, Tyr, Met, or His;
$X_8$ is Trp or D-Trp;
and
Z is —OH or —O—CH$_2$-[polystyrene resin support] with the proviso that R–$R^9$ are hydrogen when Z is —OH and $R^1$–$R^9$ are other than hydrogen when Z is —O—CH$_2$-[polystyrene resin support].

Illustrative of the applicable α-amino protecting groups represented by R are the groups:
formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxycarbonyl, tert-butyloxycarbonyl, diisopropylmethoxycarbonyl, allyloxycarbonyl, 2,2,2-trichloroethoxycarbonyl, amyloxycarbonyl, α,α-dimethylbenzylcarbonyl, α,α-dimethyl-3,5-dimethoxybenzyloxycarbonyl, benzhydryloxycarbonyl, 9-fluorenylmethoxycarbonyl, isobornyloxycarbonyl, adamantyloxycarbonyl.

Protecting groups $R^1$ and $R^9$ for the sulfhydryl group of the two cysteinyl moieties include:
benzyl, 3,4-dimethylbenzyl, p-methoxybenzyl, p-nitrobenzyl, p-chlorobenzyl, trityl, benzhydryl, tetra-hydropyranyl, acetamidomethyl, t-butyl, ethylthio, ethylcarbamoyl, benzylthiomethyl or benzoyl;

Protecting groups $R^2$ for Arg include:
nitro, tosyl, benzyloxycarbonyl, adamantyloxycarbonyl and tert-butyloxycarbonyl; preferably the tosyl group.

Protecting groups $R^2$, $R^3$ or $R^4$ for His include:
tosyl, benzyloxycarbonyl, adamantyloxycarbonyl and tert-butyloxycarbonyl; preferably the tosyl group.

Protecting groups $R^3$, or $R^4$ for Tyr include:
tert-butyl, trityl, benzyl, 2,6-dichlorobenzyl, benzyloxycarbonyl and 4-bromobenzyloxycarbonyl; preferably the 2,6-dichlorobenzyl or benzyl group.

Applicable $R^5$ protecting groups for the amino group of lysine are:
formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methylethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluorenylmethoxycarbonyl, isobornyloxycarbonyl, adamantyloxycarbonyl.

The protecting groups $R^6$, $R^7$ and $R^8$ for the hydroxyl group of the threonyl and seryl moieties, may be benzoyl, tert-butyl or benzyl. The preferred protecting group for $R^6$, $R^7$ and $R^8$ is benzyl. The selection of these protecting groups is not critical except that they must not be removed during cleavage of the α-amino protecting group during the synthesis until the peptide of the desired amino acid sequence is obtained.

The selection of such side chain amino protecting groups is not critical except that it must be one which is not removed during cleavage of the α-amino protecting group during the synthesis until the peptide of the desired amino acid sequence is obtained. Hence, the α-amino protecting and side chain amino protecting group cannot be the same.

In selecting a particular side chain protecting group to be used in the synthesis of the peptides of this invention, the following rules should be followed: (a) the protecting group must be stable to the reagent and under the reaction conditions selected for removing the α-amino protecting group at each step of the synthesis; (b) the protecting group must retain its protecting properties (i.e. not be split off under coupling conditions, and (c) the side chain protecting group must be removable under the completion of the synthesis containing the desired amino acid sequence under reaction conditions that will not alter the peptide chain.

The synthesis is commenced from the C-terminal end of the peptide by attaching α-amino protected and sulfhydryl protected cysteine to a chloromethylated resin or a hydroxymethyl resin. The preparation of the hydroxymethyl resin is described by Bodanszky et al., Chem. Ind. (London) 38, 1597–98 (1966). A chloromethylated resin is commercially available from Lab. Systems, Inc., San Mateo, Calif. and the preparation of such a resin is described by Stewart et al., "Solid Phase Peptide Synthesis" (Freeman & Co. San Francisco 1969), Chapter 1, pp. 1–6. The α-amino protected cysteine is coupled to the chloromethylated or hydroxymethyl resin with the aid of a carboxyl group activating compound such as described by Kapoor, J. Pharm. Sci. 59, pp. 1–27 (1970) the disclosure of which is incorporated herein by reference. Following the coupling of the α-amino protected cysteine to the resin support, the α-amino protecting group is removed with, for example, trifluoroacetic acid in methylene chloride, trifluoroacetic acid alone or HCl in dioxane. The deprotection is carried out at a temperature between about 0° C. and room temperature. Other standard cleaving reagents and conditions for removal of specific α-amino protecting groups may be used as described in Schroder & Lubke, "The Peptides", 1, pp. 72–75. After removal of the α-amino protecting group, the remaining α-amino protected amino acids are coupled step-wise in the desired order. However, as an alternate to adding each amino acid separately to the reaction, some of them may be coupled prior to addition to the solid phase reactor. Each protected amino acid or amino acid sequence, is introduced into the solid phase reactor in about a four-fold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid. The success of the coupling reaction at each stage of the synthesis is monitored by the ninhydrin reaction as described by E. Kaiser et al., Analyt. Biochem., 34, 595 (1970).

After the desired amino acid sequence has been synthesized, the peptide is removed from the resin support by treatment with a reagent such as hydrogen fluoride which not only cleaves the peptide from the resin but also cleaves all remaining side chain protecting groups and the α-amino protecting group R to obtain the linear product. As an alternate route, the polypeptide linked to the resin support may be separated from the resin by methanolysis after which the recovered C-terminal methyl ester is converted to the acid by hydrolysis. Any side chain protecting group may then be cleaved by the procedure previously described or by other procedures such as catalytic reduction (eg. Pd on $BaSO_4$) using conditions which will keep the Trp moiety intact. When using hydrogen fluoride for cleaving, anisole is included in the reaction vessel to prevent the oxidation of any labile amino acid (e.g. tryptophan). The linear deprotected polypeptide is converted to the cyclic disulfide by oxidation.

The solid phase synthesis procedure discussed supra, is well known in the art and has been essentially described by M. Monahan et al., C. R. Acad. Sci., Paris, 273, 508 (1971).

The following examples illustrate the preparation of the compounds of this invention.

EXAMPLE 1 tert-Butyloxycarbonyl-S-p-methoxybenzyl-L-cysteinyl-$N^g$-tosyl-L-arginyl-$N^{im}$-tosyl-L-histidyl-L-phenylalanyl-L-tryptophyl-D-tryptophyl-$N^\epsilon$-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl hydroxymethyl polystyrene ester Chloromethylated polystyrene resin was esterified with Boc-Cys(SMBzl)-OH according to Gisin, Helv. Chim. Acta., 51, 1976 (1973) and the polymeric ester was treated according to Schedule A for the incorporation of Boc-Ser(Bzl)-OH, Boc-Thr(Bzl)-OH, Boc-Phe-OH, Boc-Thr(Bzl)-OH, Boc-Lys(ClZ)-OH, Boc-D-Trp-OH, Boc-trp-OH, Boc-Phe-OH, Boc-His(Tos)-OH, Boc-Arg(Tos)-OH and Boc-Cys(SMBzl)-OH to afford the title peptidoresin.

Schedule A: (for treatment of the resin ester)

1. Wash with methylene chlorine ($CH_2Cl_2$), three times.
2. Treat with trifluoroacetic acid-methylene chloride (1:1, v/v) containing 5% 1,2-ethane dithiol for 5 minutes.
3. Repeat Step 2 for 25 minutes.
4. Wash with $CH_2Cl_2$, three times.
5. Wash with dimethylformamide (DMF).
6. Treat with 12% triethylamine in DMF for 3 minutes.
7. Wash with DMF.
8. Wash with $CH_2Cl_2$, three times.
9. Treat with 4 equivalents of the appropriate protected amino acid in $CH_2Cl_2$-DMF and stir for 5 minutes.
10. Add in two portions over a 30 minute period; 5 equivalents of diisopropylcarbodiimide dissolved in $CH_2Cl_2$. Allow reaction to procede for 6 hours.
11. Wash with DMF, three times.
12. Wash with $CH_2Cl_2$, three times.
13. Test by ninhydrin reaction according to the procedure of Kaiser et al., Annal. Biochem., 34, 595 (1970).

In case of incomplete reaction, repeat Steps 9 to 13, as above.

EXAMPLE 2

L-Cysteinyl-L-arginyl-L-histidyl-L-phenylalanyl-L-tryptophyl-D-tryptophyl-L-lysyl-L-threonyl-L-phenylalanyl-L-threonyl-L-seryl-L-cysteine cyclic (1–12) disulfide tetraacetate salt The peptidoresin of the previous example (10 g.) was mixed with 20 ml. anisole and treated with liquid HF in an ice-bath for 60 minutes with exclusion of air. The excess HF was removed under vacuo and the residue was taken in 2 N-AcOH. The polystyrene resin was filtered off and the filtrate was poured into 8 liters of deaerated water. The pH was adjusted to 7 with NH$_4$OH and the disulfhydryl compound was oxidized to the disulfide with K$_3$Fe(CN)$_6$. The pH of the solution was adjusted to 5 with glacial AcOH and then treated with Bio-Rad AG 3 and filtered. The filtrate was passed through a column of Amberlite CG 50 (H+ form) and the peptidic material which was absorbed onto the ion exchange resin was eluted with 50% aqueous AcOH. The fractions containing peptidic material were lyophilized to yield 1.34 g. of solid.

The above crude product was chromatographed through a column of Sephadex G-25 (2.5×191 cm.) and eluted with 10% aqueous AcOH. The fractions (5 ml. each) 222–251 were pooled and lyophilized to yield 305 mg. of a solid. This material was applied onto a column of Sephadex G-15 (2.5×88 cm.) and eluted with 10% aqueous AcOH to afford the title dodecapeptide, 175 mg.

TLC, Avicel precoated glass plates, chlorox-tolidine spray, Rf (BWA, 4:1:1) 0.39, Rf (BWAP, 30:24:6:20) 0.56.

Amino acid analysis: Thr (2) 1.86, Ser (1) 0.84, Phe (2) 2, Lys (1) 0.88, His (1) 1, Trp (2) 1.66, Arg (1) 0.94, Cys (N.D.).

EXAMPLE 3

L-Cysteinyl-L-arginyl-L-histidyl-L-phenylalanyl-L-histidyl-D-tryptophyl-L-lysyl-L-threonyl-L-phenylalanyl-L-threonyl-L-seryl-L-cysteine cyclic (1–12) disulfide tetraacetate salt The title dodecapeptide was prepared in the same manner as in the previous example.

TLC, Avicel precoated glass plates, chlorox-tolidine Rf (BWA, 4:1:1) 0.16, Rf (BWA, 2:1:1) 0.23, Rf (BWAP, 30:24:6:20) 0.62.

Amino acid analysis: Thr (2) 1.93, Ser (1) 0.88, Cys (2) 1.85, Phe (2) 2, Lys (1) 1.02, His (2) 1.18, Arg (1) 0.94, Trp (N.D.).

The in vivo activity of the polypeptides of this invention was established by subjecting the product of Examples 2 and 3 as representative compounds of the invention, to the following standard test procedure: Two groups of ten albino male rats were arranged to provide a control group and a group for study of the compounds of this invention. Nembutal (50 mg/kg) was injected intraperitoneally into each rat. Fifteen minutes late a subcutaneous injection of the test compound or physiological saline (control) was administered separately to each of the two groups of rats. Ten minutes later 0.5 milliliters of arginine (300 mg/ml., pH 7.2) was injected into the rats heart. The rats were decapitated five minutes later and their blood was collected in Trasylol-EDTA. Aliquot samples were radioimmunoassayed for growth hormone, insulin and glucagon. The results of these tests are presented below:

| Compound | Dose µg/kg | GH ng/ml | INS µU/ml | GLUN pg/ml |
|---|---|---|---|---|
| — | — | 202 ± 11 | 238 ± 23 | 85 ± 6 |
| Example 2 | 200 | 92 ± 8* | 149 ± 23+ | 20 ± 4* |
| — | — | 379 ± 50 | 137 ± 25 | 119 ± 8 |
| Example 2 | 50 | 104 ± 8* | 61 ± 4 | 36 ± 8* |
| — | — | 201 ± 40 | 268 ± 21 | 89 ± 14 |
| Example 3 | 100 | 48 ± 20* | 282 ± 48 | 72 ± 13 |

* = p < 0.01;
+ = p < 0.05

The procedure described in the preceding paragraph was repeated with the exception that a 2 and 4 hour period was allowed to elapse before blood sampling. The results of this test are present below:

| Compound | Dose ug/kg | Hours | GH ng/ml |
|---|---|---|---|
| — | — | 2 | 271 ± 209 |
| Example 2 | 1,000 | 2 | 51 ± 9* |
| — | — | 4 | 112 ± 17 |
| Example 2 | 1,000 | 4 | 60 ± 11+ |
| — | — | 2 | 213 ± 38 |
| Example 3 | 1,000 | 2 | 181 ± 59 |
| — | — | 4 | 150 ± 23 |
| Example 3 | 1,000 | 4 | 129 ± 29 |

* = p < 0.01;
+ = p < 0.05

Thus, the compounds of this invention suppress growth hormone release and in the case of the product of Example 2, insulin and glucagon for periods up to about four hours. These results are representative of the activities of the other compounds embraced by this invention.

The compounds of this invention are effective in the treatment of conditions involving excessive secretion of somatotropin. From the known relationship between growth hormone control in standard experimental animals and the human, the activity of the disclosed peptides characterizes them as useful in the treatment of acromegaly and diabetes where administration with or without conjoint insulin therapy improves glucose homeostasis. Administration of the peptides may be by conventional routes common to somatostatin and related polypeptides, under the guidance of a physician in an amount dictated by the extent of the dysfunction as determined by the physician. The compounds may be administered alone or in conjunction with conventional pharmaceutically acceptable carriers and adjuvants, in unit dosage form containing from about 0.05 to about 100 milligrams per kilogram host body weight.

If the active ingredient is administered in tablet form the tablet may contain: a binder such as gum tragacanth, corn starch, gelatin; an excipient such as dicalcium phosphate; a disintegrating agent such as corn starch, alginic acid, etc.; a lubricant such as magnesium stearate; and a sweetening and/or flavoring agent such as sucrose, lactose, wintergreen, etc. Suitable liquid carriers for intravenous or subcutaneous administration include isotonic saline, phosphate buffer solutions, etc.

What is claimed is:

1. A compound of the formula:

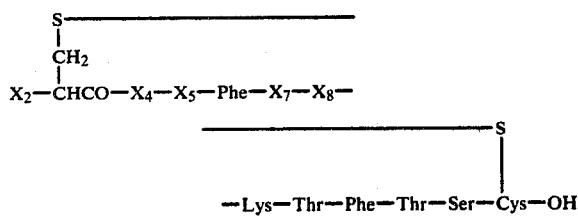

its linear precursor intermediates or non-toxic acid addition salts thereof in which $X_2$ is $NH_2$, Ala-Gly-, Ala-D-Ala, Gly-Gly-Gly-, lower alkanoyl or benzoyl;
$X_4$ is Arg, His, D-Arg, or D-His;
$X_5$ is His, Tyr, Glu, D-His, D-Tyr, or D-Glu;
$X_7$ is Trp, Tyr, Met, or His;
and
$X_8$ is Trp or D-Trp.

2. The compound of claim 1 in which $X_7$ is Trp or His.

3. The compound of claim 1 which is [des-Ala$^1$-Gly$^2$], Arg$^4$, His$^5$, His$^7$, D-Trp$^8$-somatostatin.

4. The compound of claim 1 which is [des-Ala$^1$-Gly$^2$], Arg$^4$, His$^5$, Trp$^7$, D-Trp$^8$-somatostatin.

* * * * *